United States Patent [19]
Hamamoto et al.
[11] 4,433,162
[45] Feb. 21, 1984

[54] METHOD FOR PREPARING AN ESTER OF NITROACETIC ACID

[75] Inventors: Toshikazu Hamamoto; Ryoji Sugise, both of Ube, Japan

[73] Assignee: UBE Industries, Ltd., Ube, Japan

[21] Appl. No.: 447,471

[22] Filed: Dec. 6, 1982

[30] Foreign Application Priority Data

Dec. 17, 1981 [JP] Japan ........................... 56-202545

[51] Int. Cl.$^3$ .................... C07C 76/02
[52] U.S. Cl. .................... 560/156
[58] Field of Search .................... 560/156

*Primary Examiner*—Michael L. Shippen
*Attorney, Agent, or Firm*—Frishauf, Holtz, Goodman & Woodward

[57] ABSTRACT

There is disclosed a method for preparing an ester of nitroacetic acid which comprises;

(1) a first step of subjecting a vinyl ester of a fatty acid and a nitrogen oxide to reaction with each other in the presence of a gas containing molecular oxygen in a solvent; and (2) a second step of subjecting the resultant reaction product of the first step to reaction with an alcohol.

According to the method of this invention, an ester of nitroacetic acid can effectively be obtained in higher yield.

16 Claims, No Drawings

METHOD FOR PREPARING AN ESTER OF NITROACETIC ACID

The present invention relates to a method for preparing an ester of nitroacetic acid in accordance with novel reactions.

The ester of nitroacetic acid is a compound useful as a starting material for an amino acid such as phenylalanine or tryptophane.

As for preparations of the ester of nitroacetic acid, there have heretofore been known a process of reacting an iodoacetate with silver nitrite (J. Amer. Chem. Soc., 77, 6654 (1955)), a process of reacting nitromethane with an aqueous concentrated potassium hydroxide solution and esterifying the resultant dipotassium salt of nitroacetic acid (Kogyo Kagaku Zasshi, 74, 70 (1971)), and the like. These manufacturing processes all, however, are not industrially suitable, because of poor yield of the desired product and high cost of the materials to be used.

Further, the specification of Japanese Patent Provisional Publication No. 88823/1974 discloses a method in which an ester of acetoacetic acid is reacted with an acyl nitrate in the presence of an acidic catalyst and the resultant nitroacetoacetic ester is then treated with a nucleophilic agent to prepare the ester of nitroacetic acid. According to this method, the desired product can be obtained in good yield, but it still has some industrial problems. For example, the expensive acyl nitrate is required as a nitrating agent, and since the acyl nitrate is an unstable substance having possibility of explosion, it is necessary to strictly control reaction conditions.

In view of these situations, the present inventors have researched with great zeal for the purpose of establishing an industrially advantageous method for preparing the ester of nitroacetic acid. As a result, they have found that the ester of nitroacetic acid can be manufactured extremely effectively by reacting a nitrogen oxide with a vinyl ester of a fatty acid in the presence of a gas containing molecular oxygen in a solvent and further reacting the resultant reaction product with an alcohol, and have accomplished the present invention.

According to the present invention, in the first place, a vinyl ester of a fatty acid and a nitrogen oxide are reacted with each other in the presence of a gas containing molecular oxygen in a solvent in order to obtain a precursor for the aimed ester of nitroacetic acid.

The vinyl ester of the fatty acid which is a starting material for the ester of nitroacetic acid is represented by the general formula $CH_2=CH-OCOR$, wherein R is usefully an alkyl group having 1 to 18 carbon atoms. Examples of the vinyl esters include vinyl acetate, vinyl propionate, vinyl butyrate, vinyl valerate, vinyl caproate, vinyl caprylate, vinyl caprinate, vinyl laurate, vinyl myristate, vinyl palmitate and vinyl stearate, and these esters are all easily available.

On the other hand, the useful nitrogen oxides include nitrogen monoxide, dinitrogen trioxide, nitrogen dioxide, dinitrogen tetraoxide and their equilibrium mixtures, and these oxides are materials for the manufacture of nitric acid and are available at very inexpensive cost.

Since the nitrogen oxide above tends to cause side reactions when used excessively, its amount should be controlled in the proportion of 0.1 to 20 moles, preferably 1 to 5 moles, relative to one mole of the vinyl ester of the fatty acid. Usage of the nitrogen oxide is not particularly limited, but it may be blown into the reaction system separately from or mixedly with a gas containing molecular oxygen.

The gas containing molecular oxygen to be used means oxygen, air or an oxygen-containing gas in which oxygen is optionally diluted with an inert gas such as nitrogen. The amount of the gas containing molecular oxygen is such that the oxygen in the gas is 0.5 to 50 moles, preferably 1 to 20 moles, relative to one mole of the nitrogen oxide.

Further, suitable examples of solvents to be used include acetic ester, ether, carbon tetrachloride, chloroform, methylene chloride, n-hexane and cyclohexane, which are aprotic solvents.

The reaction between the nitrogen oxide and the vinyl ester can be carried out at a temperature of −10° to 100° C., preferably −5° to 50° C., under ordinary pressure or an applied pressure.

In the second place, the reaction product prepared through the above reaction, i.e. the precursor for the desired ester of nitroacetic acid is reacted with an alcohol to obtain the nitroacetic ester which corresponds to the used alcohol.

With regard to alcohols suitable for the reaction mentioned above, aliphatic and alicyclic alcohols having 1 to 18 carbon atoms are useful. Concrete examples thereof include methanol, ethanol, propanol, butanol, pentanol, hexanol, heptanol, octanol, nonanol, decanol, dodecanol, pentadecanol, octadecanol, benzyl alcohol, phenethyl alcohol, cyclopentanol, cyclohexanol, cyclobutanol, cyclooctanol, cyclodecanol and the like. The amount of the alcohol to be used is 0.1 to 50 moles, preferably 1 to 10 moles, relative to one mole of the vinyl ester of the fatty acid.

The reaction between the aforementioned precursor and the alcohol can be carried out at a temperature of −50° to 100° C., preferably −30° to 50° C., under ordinary pressure or an applied pressure.

Further, for the purpose of increasing the yield of the aimed ester of nitroacetic acid, there can exist an additional compound below in the reaction system in an amount of 50 moles or less, preferably 0.1 to 10 moles, relative to one mole of the used alcohol. Examples of the aforementioned additional compounds include amides such as formamide, acetamide and N,N-dimethylformamide; ureas such as urea, N-methylurea, N,N-dimethylurea and thiourea; lactams such as ε-caprolactam, N-methylcaprolactam, 2-pyrrolidone, N-methyl-2-pyrrolidone and 2-piperidone; sulfoxides such as dimethyl sulfoxide and diphenyl sulfoxide; amines such as ammonia, triethylamine, pyridine, piperidine and pyrrole; oximes such as formaldoxime, acetoaldoxime and acetone oxime; and hydroxylamines such as N-methylhydroxylamine and N,N-dimethylhydroxylamine.

After the reaction, the ester of nitroacetic acid which is the aimed product can be isolated from the reaction mixture by means of a usual isolating operation such as distillation subsequent to water washing.

The reaction of this invention is supposed to proceed according to the following scheme:

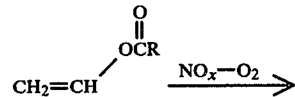

-continued

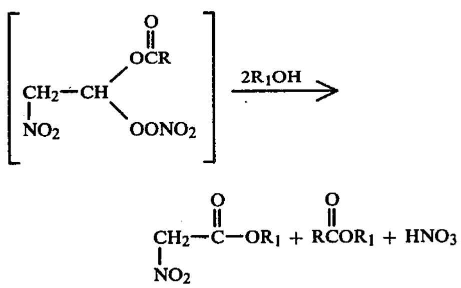

Now, the present invention will be described by way of Examples. In the Examples, the yield of an ester of nitroacetic acid in each Examples below is based on a vinyl ester of a fatty acid.

EXAMPLE 1

To a 100-ml flask equipped with a thermometer, a reflux condenser, a stirrer and a gas passage, 30 ml of ethyl acetate and 2.70 g (31.4 mmol.) of vinyl acetate were added. The contents therein were maintained at a temperature of 15° C., and 3.10 g (33.7 mmol.) of dinitrogen tetraoxide and 3020 ml (135 mmol.) of oxygen were introduced into the flask under stirring over 2 hours. A further reaction was then carried out for 10 minutes.

This reaction liquid was maintained at a temperature of 10° C., and 8.0 g (250 mmol.) of methanol was added thereto. The reaction was carried out for ten minutes under stirring and a further reaction followed at room temperature for one hour.

After completion of the reaction, the reaction mixture was subjected to a gas-chromatographic analysis. Obtained results indicate that 1.98 g (yield: 53%) of methyl nitroacetate was produced.

EXAMPLES 2 AND 3

Experiments were carried out in the same manner as in Example 1 with the exception that vinyl propionate (Example 2) and n-vinyl butyrate (Example 3) were used respectively in place of the vinyl acetate in an amount of 31.4 mmol.

EXAMPLES 4 TO 6

Experiments were carried out in the same manner as in Example 1 with the exception that the respective solvents recited in Table 1 below were used in place of the ethyl acetate in an amount of 30 ml.

Results of Examples 1 to 6 are set out in Table 1:

TABLE 1

| Example | Vinyl ester of fatty acid | Solvent | Yield of methyl nitroacetate (%) |
|---|---|---|---|
| 1 | Vinyl acetate | Ethyl acetate | 53 |
| 2 | Vinyl propionate | Ethyl acetate | 52 |
| 3 | n-Vinyl butyrate | Ethyl acetate | 50 |
| 4 | Vinyl acetate | Carbon tetrachloride | 45 |
| 5 | Vinyl acetate | Methylene chloride | 47 |
| 6 | Vinyl acetate | Chloroform | 47 |

EXAMPLES 7 TO 11

Experiments were carried out in the same manner as in Example 1 with the exception that the respective alcohols recited in Table 2 were used in place of the methanol in an amount of 250 mmol.

Results of Examples 7 to 11 are set out in Table 2 below:

TABLE 2

| Example | Alcohol | Product (Ester of nitroacetic acid) | Yield (%) |
|---|---|---|---|
| 7 | Ethanol | Ethyl nitroacetate | 51 |
| 8 | n-Propanol | n-Propyl nitroacetate | 40 |
| 9 | n-Butanol | n-Butyl nitroacetate | 35 |
| 10 | Benzyl alcohol | Benzyl nitroacetate | 45 |
| 11 | Cyclohexyl alcohol | Cyclohexyl nitroacetate | 35 |

EXAMPLE 12

To the same flask as in Example 1, 30 ml of ethyl acetate and 2.70 g (31.4 mmol.) of vinyl acetate were added. The contents therein were maintained at a temperature of 15° C., and 1510 ml (67.4 mmol.) of nitrogen monoxide and 3775 ml (169 mmol.) of oxygen were introduced into the flask under stirring over 2 hours. A further reaction was then carried out for 10 minutes.

This reaction mixture was maintained at a temperature of 0° C., and a mixed solution of 10.0 g (313 mmol.) of methanol and 8.0 g (110 mmol.) of N,N-dimethylformamide was added to the mixture. The reaction was carried out for ten minutes under stirring and a further reaction followed at room temperature for one hour. After completion of the reaction, the reaction mixture was subjected to a gas-chromatographic analysis. According to obtained results, it was found that 2.72 g (yield: 73%) of methyl nitroacetate was produced.

EXAMPLES 13 TO 15

Experiments were carried out in the same manner as in Example 12 with the exception that the respective additives recited in Table 3 below were used in place of the N,N-dimethylformamide in an amount of 110 mmol.

TABLE 3

| Example | Additive | Yield of methyl nitroacetate (%) |
|---|---|---|
| 12 | N,N—Dimethylformamide | 73 |
| 13 | Dimethyl sulfoxide | 72 |
| 14 | N—Methyl-ε-caprolactam | 72 |
| 15 | Urea | 70 |

EXAMPLE 16

To an autoclave, 60 ml of ethyl acetate and 5.40 g (62.8 mmol.) of vinyl acetate were added. The contents therein were maintained at a temperature of 15° C., and oxygen was introduced thereinto with the aid of pressure so as to reach 7 $Kg/cm^2G$. Then, 135 mmol. of nitrogen monoxide was introduced thereinto under pressure over 3 hours. After release of the autoclave, the reaction mixture was maintained at 10° C., and 16.0 g (500 mmol.) of methanol was added thereto, followed by stirring for ten minutes at the same temperature and further for one hour at room temperature.

After completion of the reaction, the reaction mixture was subjected to a gas-chromatographic analysis. According to obtained results, it was found that 4.67 g (yield: 63%) of methyl nitroacetate was produced.

We claim:

1. A method for preparing an ester of nitroacetic acid which comprises;

(1) a first step of subjecting a vinyl ester of a fatty acid and a nitrogen oxide to reaction with each other in the presence of a gas containing molecular oxygen in a solvent; and (2) a second step of subjecting the resultant reaction product of the first step to reaction with an alcohol.

2. A method as claimed in claim 1, wherein the amount of said nitrogen oxide is in the range of 0.1 to 20 moles relative to one mole of the vinyl ester of the fatty acid.

3. A method as claimed in claim 2, wherein the amount of said nitrogen oxide is in the range of 1 to 5 moles relative to one mole of the vinyl ester of the fatty acid.

4. A method as claimed in claim 1, wherein the amount of said gas containing molecular oxygen is in the range of 0.5 to 50 moles in terms of oxygen, relative to one mole of the nitrogen oxide.

5. A method as claimed in claim 4, wherein the amount of said gas containing molecular oxygen is in the range of 1 to 20 moles in terms of oxygen, relative to one mole of the nitrogen oxide.

6. A method as claimed in claim 1, wherein said solvent is an aprotic solvent.

7. A method as claimed in claim 6, wherein said solvent is an aprotic solvent selected from the group consisting of acetic acid, ether, carbon tetrachloride, chloroform, methylene chloride, n-hexane and cyclohexane.

8. A method as claimed in claim 1, wherein the reaction of the first step is conducted at a temperature of −10° to 100° C.

9. A method as claimed in claim 8, wherein the reaction of the first step is conducted at a temperature of −5° to 50° C.

10. A method as claimed in claim 1, wherein the amount of the said alcohol is in the range of 0.1 to 50 moles relative to one mole of the vinyl ester of the fatty acid.

11. A method as claimed in claim 10, wherein the amount of said alcohol is in the range of 1 to 10 moles relative to one mole of the vinyl ester of the fatty acid.

12. A method as claimed in claim 1, wherein the reaction of the second step is conducted at a temperature of −50° to 100° C.

13. A method as claimed in claim 12, wherein the reaction of the second step is conducted at a temperature of −30° to 50° C.

14. A method as claimed in claim 1, wherein reaction of the second step is conducted in the presence of an accelerator selected from the group consisting of amides, ureas, lactams, sulfoxides, amines, oximes and hydroxylamines.

15. A method as claimed in claim 14, wherein the amount of said accelerator is 50 moles or less relative to one mole of the alcohol.

16. A method as claimed in claim 15, wherein the amount of said accelerator is in the range of 0.1 to 10 moles relative to one mole of the alcohol.

* * * * *